United States Patent
Mallard et al.

(10) Patent No.: US 8,568,704 B2
(45) Date of Patent: *Oct. 29, 2013

(54) DERMATOLOGICAL/PHARMACEUTICAL COMPOSITIONS COMPRISING BENZOYL PEROXIDE, AT LEAST ONE NAPHTHOIC ACID COMPOUND AND AT LEAST ONE POLYURETHANE POLYMER

(75) Inventors: Claire Mallard, Mougins (FR); Emmanuelle At, Antibes (FR)

(73) Assignee: Galderma Research & Development, Biot (FR)

( * ) Notice: Subject to any disclaimer, the term of this patent is extended or adjusted under 35 U.S.C. 154(b) by 303 days.

This patent is subject to a terminal disclaimer.

(21) Appl. No.: 12/453,968

(22) Filed: May 28, 2009

(65) Prior Publication Data

US 2010/0143285 A1 Jun. 10, 2010

Related U.S. Application Data

(63) Continuation of application No. PCT/FR2007/052412, filed on Nov. 28, 2007.

(30) Foreign Application Priority Data

Nov. 28, 2006 (FR) ...................................... 06 55138

(51) Int. Cl.
*A61K 31/33* (2006.01)

(52) U.S. Cl.
USPC ...................... 424/78.03; 424/400; 424/78.02

(58) Field of Classification Search
None
See application file for complete search history.

(56) References Cited

U.S. PATENT DOCUMENTS

| 3,535,422 | A | * | 10/1970 | Cox et al. ...................... 514/714 |
| 4,387,107 | A | | 6/1983 | Klein et al. |
| 6,358,541 | B1 | * | 3/2002 | Goodman ...................... 424/727 |
| 7,998,467 | B2 | * | 8/2011 | Mallard et al. ............. 424/78.03 |
| 2003/0147977 | A1 | | 8/2003 | Goodman |
| 2008/0181963 | A1 | * | 7/2008 | Orsoni et al. ................. 424/489 |
| 2008/0253986 | A1 | | 10/2008 | Mallard et al. |

FOREIGN PATENT DOCUMENTS

| EP | 0299758 A2 | 1/1989 |
| FR | 2462424 | 2/1981 |
| FR | 2833841 A1 | 6/2003 |
| FR | 2890861 A1 | 3/2007 |
| WO | WO 03/075908 A1 | 9/2003 |

OTHER PUBLICATIONS

Kang et al. "Assessment of adapalene gel for the treatment of actinic keratoses and lentigines: A randomized trial", J Am Acad Dermatol., Jul. 2003, pp. 83-90, vol. 49, No. 1.
Wolf "An update of recent clinical trials examining adapalene and acne", European Academy of Dermatology and Venereology, 2001, pp. 23-29, vol. 15, Supp. 3.
Korkut et al., Benzoyl Peroxide, Adapalene, and Their Combination in the Treatment of Acne Vulgaris, The Journal of Dermatology, 2005, pp. 169-173, vol. 32.
Martin et al., "Chemical stability of adapalene and tretinoin when combined with benzoyl peroxide in presence and in absence of visible light and ultraviolet radiation", British Journal of Dermatology, 1998, pp. 8-11, vol. 139, Supp. 52.

* cited by examiner

*Primary Examiner* — Anand Desai
*Assistant Examiner* — Melissa Mercier
(74) *Attorney, Agent, or Firm* — Dentons US LLP

(57) ABSTRACT

Topically applicable, dermatological/pharmaceutical compositions contain, formulated into a physiologically acceptable medium, benzoyl peroxide, at least one naphthoic acid compound and at least one compound of the polyurethane polymer type or derivatives thereof, wherein the benzoyl peroxide and the at least one naphthoic acid compound are dispersed therein.

27 Claims, No Drawings

DERMATOLOGICAL/PHARMACEUTICAL COMPOSITIONS COMPRISING BENZOYL PEROXIDE, AT LEAST ONE NAPHTHOIC ACID COMPOUND AND AT LEAST ONE POLYURETHANE POLYMER

CROSS-REFERENCE TO PRIORITY/PCT APPLICATIONS

This application claims priority under 35 U.S.C. §119 of FR 06/55138, filed Nov. 28, 2006, and is a continuation of PCT/FR 2007/052412, filed Nov. 28, 2007 and designating the United States (published in the French language on Jun. 5, 2008 as WO 2008/065306 A1; the title and abstract were also published in English), each hereby expressly incorporated by reference in its entirety and each assigned to the assignee hereof.

BACKGROUND OF THE INVENTION

1. Technical Field of the Invention

The present invention relates to compositions for topical administration, and their applications as cosmetic or pharmaceutical products, such compositions being particularly useful for the treatment of acne.

2. Description of Background and/or Related and/or Prior Art

Acne is a frequent multifactorial pathology which affects skin rich in sebaceous glands (face, scalpular region, arms and intertriginous regions). It is the most frequent of the dermatoses. The following five pathogenic factors play a decisive role in the constitution of acne:

1. genetic predisposition;
2. overproduction of sebum (seborrhoea);
3. androgens;
4. follicular keratinization disorders (comedogenesis); and
5. bacterial colonization and inflammatory factors.

There are several forms of acne, which all have in common the impairment of the pilosebaceous follicles. There may be mentioned in particular acne conglobata, acne keloid of the nape of the neck, acne medicamentosa, recurrent miliary acne, acne necrotica, acne neonatorum, premenstrual acne, occupational acne, acne rosacea, senile acne, solar acne and acne vulgaris.

Acne vulgaris, also called polymorphic juvenile acne, is the most common. It comprises four stages, but passage through all the stages is not obligatory:

Stage 1 corresponds to comedonal acne characterized by a large number of open and/or closed comedones, and of microcysts.

Stage 2, or papulopustular acne, is of mild to moderate seriousness. It is characterized by the presence of open and/or closed comedones, of microcysts, but also of red papules and of pustules. It affects mainly the face and leaves few scars.

Stage 3, or papulocomedonal acne, is more serious and extends to the back, to the thorax and to the shoulders. It is accompanied by a larger number of scars.

Stage 4, or nod ulocystic acne, is accompanied by numerous scars. It has nodules as well as large purplish and painful pustules.

The various forms of acne described above may be treated with active agents such as anti-seborrhoeic agents and anti-infective agents, for example benzoyl peroxide (in particular the product Eclaran® marketed by Pierre Fabre), with retinoids such as tretinoin (in particular the product Retacnyl® marketed by Galderma) and isotretinoin (the product Roaccutane® marketed by Laboratoires Roche), or with naphthoic acid derivatives. Naphthoic acid derivatives such as in particular 6-[3-(1-adamantyl)-4-methoxyphenyl]-2-naphthoic acid, commonly called adapalene (the product Differine® marketed by Galderma), are widely described and recognized as active ingredients that are as effective as tretinoin for the treatment of acne.

The combination of several local treatments (antibiotics, retinoids, peroxides, zinc) is also used in dermatology to make it possible to enhance the efficacy of the active ingredients and to reduce their toxicity (Cunliffe W. J., *J. Dermatol. Treat.*, 2000, 11 (suppl2), pgs. 13-14).

The multiple application of different dermatological products may be quite cumbersome and demanding for the patient.

Therefore, one must understand the importance of developing a novel treatment that is effective on dermatological conditions in a stable composition offering a good cosmetic property and allowing a single application and a pleasant use for the patient.

Among this range of therapies proposed by one skilled in the art, nothing has encouraged the combination, in the same composition, benzoyl peroxide and a retinoid.

However, the formulation of such a composition poses several problems.

First of all, the efficacy of benzoyl peroxide is linked to its decomposition when it is brought into contact with the skin. Indeed, it is the oxidizing properties of the free radicals produced during this decomposition which lead to the desired effect. Accordingly, to maintain optimum efficacy of the benzoyl peroxide, it is important to prevent its decomposition before administration, that is to say during storage.

Now, benzoyl peroxide is an unstable chemical compound, which makes its formulation in finished products difficult.

The solubility and stability of benzoyl peroxide have been studied by Chellquist et al. in ethanol, propylene glycol and various mixtures of polyethylene glycol 400 (PEG 400) and water (Chellquist E. M. and Gorman W. G., *Pharm. Res.*, 1992, Vol 9: 1341-1346).

Benzoyl peroxide is particularly soluble in PEG 400 and ethanol as the following table shows:

| Solvent | Solubility of benzoyl peroxide (mg/g) |
| --- | --- |
| PEG 400 | 39.6 |
| Ethanol | 17.9 |
| Propylene glycol | 2.95 |
| Propylene glycol/water (75:25) | 0.36 |
| Glycerol | 0.15 |
| Water | 0.000155 |

This document moreover specifies that the stability of benzoyl peroxide is greatly influenced by the chemical composition of the formulation and by the storage temperature. Benzoyl peroxide is extremely reactive and is degraded in solution at low temperature because of the instability of its peroxide bond.

The authors thus observed that benzoyl peroxide in solution is degraded more or less rapidly in all the solvents studied depending on the type of solvent and its concentration.

The benzoyl peroxide degradation time in PEG 400 (0.5 mg/g), in ethanol and in propylene glycol are respectively 1, 4, 29 and 53 days at 40° C. Such a degradation does not allow the preparation of a product useful for sale.

Thus, to limit the problem of rapid instability of benzoyl peroxide in solution, it was found to be advantageous to formulate the benzoyl peroxide in dispersed form. However, this type of formulation is not completely satisfactory since degradation of benzoyl peroxide is still observed in the finished product.

Another difficulty that has to be overcome for the preparation of a composition comprising both benzoyl peroxide and a retinoid is that most retinoids are particularly sensitive to natural oxidation, to visible light and to ultraviolet radiation, and benzoyl peroxide being a strong oxidant, the chemical compatibility of these compounds in the same formulation poses numerous problems of stability from the physical and chemical point of view.

A study of stability of two retinoids was carried out by combining two commercial products, one containing a retinoid (tretinoin or adapalene) and the second based on benzoyl peroxide (B. Martin et al., *Br. J. Dermatol.*, (1998) 139, (suppl. 52), 8-11).

The presence of the benzoyl peroxide-based formulation causes a very rapid degradation of the oxidation-sensitive retinoids: measurement shows that 50% of the tretinoin is degraded within 2 hours, and 95% within 24 hours. In the composition in which the retinoid is adapalene, no degradation of adapalene was measured for 24 hours. This study confirms that benzoyl peroxide is degraded and degrades oxidation-sensitive retinoids over time by gradually releasing benzoic acid into finished products.

Now, it is clear that the degradation of benzoyl peroxide and of retinoids is not desirable since it damages the efficacy of the composition containing them.

Nothing has encouraged the combination of these two active agents to obtain a stable composition of the emulsion type given that it was commonly known that the presence of benzoyl peroxide chemically and physically destabilized this type of composition.

Furthermore, it was sought to develop compositions which make it possible to enhance the topical penetration of certain active agents by incorporating, into compositions, compounds of the polyurethane polymer type or derivatives thereof (EP-0,299,758). The product Avita®, marketed by BERTEK Pharmaceuticals Inc., is an example thereof. It contains in particular 0.025% by weight of tretinoin, relative to the total weight of the composition, solubilized in compositions of the gel or cream type and containing polyurethane polymers (type 2 polyolprepolymers marketed by Bertek Pharmaceuticals Inc.) to limit desquamation, irritation and drying of the skin.

SUMMARY OF THE INVENTION

It has now surprisingly been demonstrated, that polyurethane polymers can promote topical penetration of compounds that are insoluble, dispersed or suspended in pharmaceutical compositions, such as in particular benzoyl peroxide and naphthoic acid derivatives.

Taking the above into consideration, one problem which the present invention solves is the formulation of compositions that are stable and less irritant than those of the prior art, comprising a combination of benzoyl peroxide with at least one naphthoic acid compound, the active agents being in dispersed form, and at least one compound of the polyurethane polymer type or derivatives thereof, said compositions promoting the topical penetration of the active ingredients in dispersed form.

Accordingly, the present invention features compositions, preferably pharmaceutical compositions, in particular for topical application, comprising, formulated into a physiologically acceptable medium, at least:
(i) benzoyl peroxide,
(ii) a naphthoic acid compound, and
(iii) a compound of the polyurethane polymer type or derivatives thereof, the said naphthoic acid compound and the said benzoyl peroxide being in a dispersed form in the said compositions.

The expression active agent in dispersed form according to the invention means an active agent in the form of solid particles, suspended in a given vehicle. Such particles have in particular a size greater than 10 µm.

Advantageously, the retinoid and benzoyl peroxide particle size distribution is such that at least 80% of the particles in numerical terms, and preferably at least 90% of the particles in numerical terms, have a diameter less than 25 µm and at least 99% of the particles in numerical terms have a diameter less than 100 µm.

The expression "physiologically acceptable medium" means a medium compatible with the skin, the mucous membranes and/or the superficial body growths.

The present invention also features formulation of pharmaceutical compositions useful for the treatment and/or prevention of dermatological conditions or afflictions associated with a keratinization disorder relating to cell differentiation and proliferation, and in particular for treating pathologies selected from among acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, polymorphic acne, acne rosacea, senile acne, solar acne and acne medicamentosa.

The compositions according to the invention comprises benzoyl peroxide, at least one naphthoic acid compound, and at least one compound of the polyurethane polymer type or derivatives thereof.

DETAILED DESCRIPTION OF BEST MODE AND SPECIFIC/PREFERRED EMBODIMENTS OF THE INVENTION

Naphthoic acid is a compound of formula:

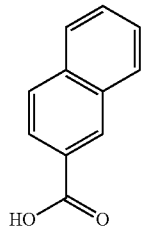

The expression naphthoic acid derivative means compounds of formula (I):

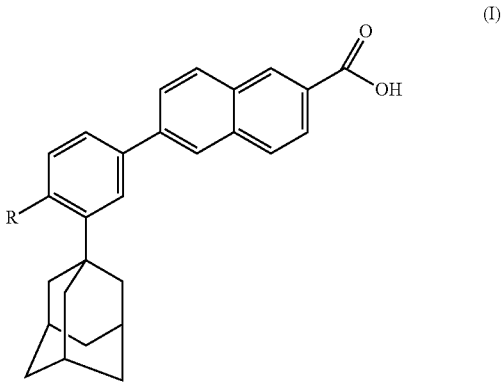

in which:

R is a hydrogen atom, a hydroxyl radical, a branched or unbranched alkyl radical having from 1 to 4 carbon atoms, an alkoxy radical having from 1 to 10 carbon atoms or a cycloaliphatic radical that is substituted or unsubstituted.

The expression linear or branched alkyl radical having from 1 to 4 carbon atoms means, preferably, methyl, ethyl, propyl or butyl radicals.

The expression alkoxy radical having from 1 to 10 carbon atoms means, preferably, methoxy, ethoxy, propoxy, butoxy, hexyloxy or decyloxy radicals.

The expression cycloaliphatic radical means, preferably, mono- or polycyclic radicals such as the 1-methylcyclohexyl radical or the 1-adamantyl radical.

derivatives thereof. The expression polyurethane polymers means polyalkylene glycols as described in EP0299758, and marketed by Bertek Pharmaceuticals Inc. The polyurethane polymers according to the invention have unique properties which confer advantageous properties on them for applications in the cosmetics and pharmaceutical fields. Indeed, the polyurethane polymers significantly influence the deposition of certain agents on and in the skin, by virtue of their high molecular weight. Furthermore, the polyurethane polymers preferably remain in the top layers of the skin.

Among the polyurethane polymers formulated into the compositions according to the invention, exemplary are the polyurethane polymers of general formula:

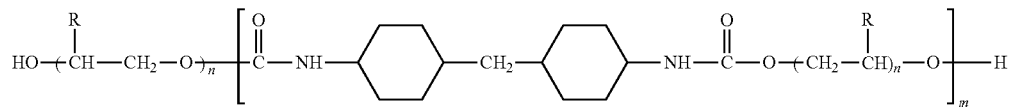

Among the naphthoic acid compounds formulated into the compositions according to the invention, there will be advantageously selected 6-[3-(1-adamantyl)-4-methoxyphenyl]-2-naphthoic acid (adapalene), 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid.

The abovementioned naphthoic acid compounds are generally provided in a dispersed form in the compositions according to the invention. The insoluble naphthoic acid compounds are thus homogeneously distributed in the composition according to the invention.

In the compositions according to the invention, the naphthoic acid compounds are included at concentrations of less than or equal to 10% by weight relative to the total weight of the composition, and preferably from 0.001% to 10% by weight relative to the total weight of the composition, and preferably from 0.01% to 5%, more preferably from 0.03% to 2%, and most preferably of 0.1% to 0.3% by weight relative to the total weight of the composition.

Herein, unless otherwise specified, it is understood that when concentration ranges are given, they include the top and bottom ends of the said range.

Advantageously, the naphthoic acid compound contained in the compositions according to the invention is 6-[3-(1-adamantyl)-4-methoxyphenyl]-2-naphthoic acid (adapalene). The adapalene concentration in the compositions according to the invention is then from 0.01% to 0.5%, more preferably from 0.05% to 0.03% to from 0.1% to 0.3%, in particular a concentration of 0.1% to a concentration of 0.3%.

In the compositions according to the invention, benzoyl peroxide is employed at concentrations ranging from 1 to 10% by weight, more particularly from 2 to 7% by weight, more preferably still from 2.5 to 5% by weight relative to the total weight of the composition.

Benzoyl peroxide may also be employed in free form or alternatively in an encapsulated form in a form adsorbed onto, or absorbed into, any porous support.

This may be for example benzoyl peroxide encapsulated into a polymer system consisting of porous microspheres, such as for example microsponges marketed under the trademark Microsponges P009A Benzoyl peroxide by Cardinal Healthcare.

The compositions according to the invention additionally comprise compounds of the polyurethane polymer type or in which:

R is CH3 or H;

n is an integer selected such that the polyurethane polymer has a molecular mass at least equal to 1,000, advantageously, n is from 5 and 55;

and m is a number ranging from 1 to 6 inclusive.

Examples of polyurethane polymers suited for the compositions according to the invention, taken alone or as a mixture, include polyolprepolymer-2 (PP-2) and polyolprepolymer-14 (PP-14) (called poly[oxy(methyl-1,2-ethanediyl), αα hydro-ω-hydroxy-, polymer with 1,1'-methylene-bis[4-isocyanatocyclohexane]), and polyolprepolymer-15 (PP-15) (called poly(oxy-1,2-ethanediyl), α-hydro-ω-hydroxy-, polymer with 1,1'-methylene-bis[4-isocyanatocyclohexane]) taken alone or as a mixture. These three polymers are marketed by Bertek Pharmaceuticals Inc., and correspond to the general formula above with m varying from 1 to 4 and for which, respectively, n=12 for PP-2, n=51 for PP-14 and n=8 for PP-15.

Among the polyurethane polymers suitable for the compositions according to the invention, polyolprepolymer-2 (PP-2) will be advantageously selected.

In the compositions according to the invention, compounds of the polyurethane polymer type or derivatives thereof are included at concentrations less than or equal to 20%, preferably from 0.5% to 20% by weight relative to the total weight of the composition, and more preferably from 1% to 10%, preferably at a concentration less than 7% to in particular 1%, 3% or 5%. Such low concentrations of polyurethane polymers advantageously make it possible to reduce the toxicity and the general irritation of the compositions according to the invention.

The polyurethane polymers in the compositions according to the invention have anti-irritant and moisturizing properties which are particularly advantageous in the case of the adapalene and benzoyl peroxide formulations. Indeed, the naphthoic acid compounds and the benzoyl peroxide may be irritant and may have a drying action on the skin. It is therefore advantageous to reduce the irritation induced to be able to increase the doses.

The compositions of the present invention may be provided in any of the galenic forms normally used for a topical application, in particular in the form of aqueous, aqueous-alcoholic or oily dispersions, of dispersions of the lotion type, of aqueous, anhydrous or lipophilic gels, of emulsions with a liquid or semiliquid consistency of the milk type, which are obtained by dispersing a fatty phase in an aqueous phase (O/W) or conversely (W/O), or of suspensions or emulsions with a soft, semiliquid or solid consistency of the cream, gel cream or ointment type, or alternatively of microemulsions, microcapsules, microparticles or vesicular dispersions of the ionic and/or nonionic type.

Preferably, the compositions according to the invention are provided in the form of lotions, gel creams, gels or creams.

One skilled in the art will take care to select the excipients constituting the compositions according to the invention according to the desired galenic form and such that the advantageous properties of the composition according to the invention are preserved.

The compositions according to the invention may further comprise one or more of the following ingredients:
 a) one or more gelling agents or suspending agents,
 b) one or more chelating agents,
 c) one or more wetting agents,
 d) one or more preservatives,
 e) one or more emulsifiers,
 f) one or more wetting surfactants,
 g) one or more lipophilic excipients constituting the fatty phase,
 h) an aqueous phase,
 i) one or more additives.

In one of the preferred embodiments of the invention, the composition is provided in the form of a gel. In a preferred embodiment, the gelling agents used for carrying out the invention are pH-independent agents.

The expression pH-independent gelling agent means a gelling agent capable of conferring sufficient viscosity on the composition to maintain the retinoid and the benzoyl peroxide in suspension, even under the influence of a pH variation due to the release of benzoic acid by the benzoyl peroxide.

Examples of gelling agents or suspending agents which may comprise the compositions according to the invention are acrylates/C10-30 Alkyl Acrylate Crosspolymer marketed under the trademark Pemulen TR-1 or Pemulen TR-2 by Noveon, Avicel CL-611 marketed by FMC Biopolymer, so-called electrolyte-insensitive carbomers marketed under the trademark Ultrez 20®, 1382 or Carbopol ETD2020NF® by Noveon, polysaccharides with, by way of non-limiting examples, xanthan gum such as Xantural 180® marketed by Kelco, guar gum, chitosans, cellulose and its derivatives such as hydroxypropylmethylcellulose in particular the product marketed under the trademark Methocel E4M premium by Dow Chemical or hydroxyethylcellulose, in particular the product marketed under the trademark Natrosol HHX 250® by Aqualon, the family of aluminum magnesium silicates such as Veegum K marketed by Vanderbilt, the family of acrylic polymers coupled to hydrophobic chains such as PEG-150/decyl/SMDI copolymer marketed under the trademark Aculyn 44 (polycondensate comprising at least, as components, a polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%)), the family of modified starches such as modified potato starch marketed under the trademark Structure Solanace or alternatively mixtures thereof and gelling agents of the family of polyacrylamides such as the Sodium acryloyldimethyltaurate copolymer/isohexadecane/polysorbate 80 mixture marketed under the trademark Simulgel 600 PHA by Seppic, the polyacrylamide/isoparaffin C13-14/laureth-7 mixture such as, for example, that marketed under the trademark Sepigel 305 by Seppic, the family of carrageenans which are in particular divided into four broad families: κ, λ, β, ω such as Viscarin® and Gelcarin® which are marketed by IMCD.

The gelling agent as described above may be incorporated at preferred concentrations ranging from 0.1 to 15%, and more preferably ranging from 0.5 to 5%.

As preferred gelling agents, exemplary are carbomers, polyacrylamides, acrylic polymers coupled to hydrophobic chains, cellulose and its derivatives such as hydroxypropylmethylcellulose or hydroxyethylcellulose; polysaccharides and in particular xanthan gum, and in particular those marketed in particular under the trademarks Simulgel 600, PEG-150/decyl/SMDI copolymer, Methocel E4M premium, Natrosol HHX 250®, Xantural 180® Carbopol Ultrez 20.

Among the chelating agents, examples are ethylenediaminetetraacetic acid (EDTA), diethylenetriaminepentaacetic acid (DTPA), ethylenediaminedi(O-hydroxyphenylacetic acid) (EDDHA), 2-hydroxyethylenediaminetriacetic acid (HEDTA), ethylenediaminedi(β-hydroxy-p-methylphenyl) acetic acid (EDDHMA) and ethylenediaminedi(5-carboxy-2-hydroxyphenyl)acetic acid (EDDCHA).

As preferred chelating agent, exemplary is ethylenediaminetetraacetic acid (EDTA) marketed in particular under the trademark Titriplex III®.

Among the wetting agents which have the role of reducing the surface tension and allowing greater spreading of the liquid, exemplary are compounds such as propylene glycol, dipropylene glycol, propylene glycol dipelargonate, lauroglycol and ethoxydiglycol, ethylene oxide and propylene oxide block copolymers such as those marketed under the trademark Synperonic PE/L44, Synperonic PE/L62, alone or as a mixture.

A preferred wetting agent is propylene glycol.

Among the preservatives, exemplary are benzoic acid and its derivatives with benzyl alcohol, benzalkonium chloride, sodium benzoate, bronopol, chlorhexidine, chlorocresol and its derivatives, ethyl alcohol, phenethyl alcohol, phenoxyethanol, potassium sorbate, diazolidinylurea, parabens such as propylparaben or methylparaben, taken alone or as mixtures.

As preferred preservatives, exemplary are parabens and phenoxyethanol or benzalkonium chloride, alone or as a mixture.

The compositions according to the invention may comprise one or more emulsifiers.

The surfactant emulsifiers are amphiphilic compounds which possess a hydrophobic part having affinity for oil and a hydrophilic part having affinity for water, thus creating a link between the two phases. The ionic or nonionic emulsifiers therefore stabilize the oil/water emulsions by being adsorbed at the interface and by forming lamellar layers of liquid crystals.

The emulsifying power of the nonionic surfactants is closely linked to the polarity of the molecule. This polarity is defined by the HLB (Hydrophilic/Lipophilic Balance).

A high HLB indicates that the hydrophilic fraction is predominant and, conversely, a low HLB indicates that the lipophilic part is predominant. For example, HLB values greater than about 10 correspond to hydrophilic surfactants.

Surfactants may be classified, according to their structure, under the generic terms "ionic" (anionic, cationic, amphoteric) or "nonionic". The nonionic surfactants are surfactants which do not dissociate into ions in water and are therefore insensitive to pH variations.

The nonionic surfactants are particularly well suited for the preparation of oil-in-water type emulsions which are the subject of the present invention. Thus, the emulsifying system, constituting the emulsion of the invention, comprises at least one nonionic surfactant, containing a predominant hydrophilic fraction, that is to say having a high HLB, greater than about 10.

Examples of nonionic surfactants having a high HLB are sorbitan esters such as PEO(20) sorbitan monooleate, marketed under the trademark "Tween 80" (HLB=15); PEO(20) sorbitan monostearate marketed under the trademark "Tween 60" (HLB=14.9); fatty alcohol ethers such as PEO(21) stearyl ether (HLB=15.5), or ceteareth 20 marketed under the trademark "Eumulgin B2" by Cognis (HLB of 15.5).

Preferably, the said nonionic surfactants with a high HLB have a HLB of from 10 and 18.

Examples of nonionic surfactants with a low HLB (which are lipophilic) are sorbitan esters, such as sorbitan monostearate (marketed under the trademark Span 60 by Uniqema), glycerol esters (marketed under the trademark Cutina GMS-VPH by Cognis) such as glycerol monostearate (Cutina GMS from Cognis), sucrose esters with a low HLB such as sucrose distearate.

Preferably, the said nonionic surfactants with a low HLB have an HLB of less than 10.

The nonionic surfactants may be employed alone or as a mixture of two of them or more to form the emulsifying system constituting the emulsion of the invention.

Preferably, one or more "nonionic surfactant with a high HLB"/"nonionic surfactant with a low HLB" pairs will be employed as emulsifying system; this may be in particular a nonionic emulsifying system comprising at least one nonionic surfactant having an HLB greater than about 10 and at least one nonionic surfactant having an HLB of less than about 10.

The ratio of each of the two surfactants forming the abovementioned pair is determined most often by calculating the HLB required for the fatty phase used.

As preferred emulsifiers, exemplary are hydrophilic emulsifiers such as Tween 80, Glyceryl Monostearate & POE Stearate marketed under the trademark Arlacel 165FL® by Uniqema; PEG 6 stearate and PEG 32 stearate marketed under the trademark TEFOSE 1500 by GATTEFOSSE, lipophilic emulsifiers such as Glucate SS (methyl glucose sesquistearate) and Glucamate SSE 20 (PEG 20 methyl glucose sesquistearate) marketed by Amerchol, Polyoxyethylene (21) Stearyl Ether marketed under the trademark Brij721® by Uniqema.

The compositions according to the invention may also comprise a fatty phase. This fatty phase may comprise for example vegetable, mineral, animal or synthetic oils, silicone oils and mixtures thereof.

Examples of mineral oils include paraffin oils of different viscosities such as Primol 352®, Marcol 82®, Marcol 152® marketed by Esso.

As vegetable oil, exemplary are sweet almond oil, palm oil, soybean oil, sesame oil and sunflower oil.

As animal oil, exemplary are lanolin, squalene, fish oil, mink oil with as derivative the squalane marketed under the trademark Cosbiol® by Laserson.

As synthetic oil, exemplary are an ester such as cetearyl isononanoate such as the product marketed under the trademark Cetiol SNPH® by Cognis France, diisopropyl adipate such as the product marketed under the trademark Ceraphyl 230® by ISF, isopropyl palmitate such as the product marketed under the trademark Crodamol IPP® by Croda, caprylic capric triglyceride such as Miglyol 812® marketed by Huls/Lambert Rivière.

As volatile or nonvolatile silicone oil, exemplary are dimethicone such as the product marketed under the trademark Q7-9120 Silicone fluid with a viscosity of 20 cst to 12 500 cst or the product marketed under the trademark ST-Cyclomethicone 5NF® by Dow Corning.

It is also possible to add solid fatty substances such as natural or synthetic waxes. In this case, one skilled in the art will adjust the heating temperature for the preparation depending on the presence or absence of these solids.

For the compositions according to the invention, mineral oils and silicone oils and more particularly Marcol 152® and ST-Cyclomethicone 5 NF are preferred.

The compositions according to the invention may also comprise emollient agents. Examples of emollient agents include glycerine, sorbitol, sugars (by way of example glucose, lactose), PEGs (by way of example Lutrol E400), urea, amino acids (by way of example serine, citrulline, alanine).

The compositions of the invention may further comprise any additive customarily used in the cosmetics or pharmaceutical field, such as surfactants, neutralizing agents (by way of example, triethanolamine, 10% sodium hydroxide solution, citric acid/sodium citrate buffer, succinic acid/sodium succinate buffer), sunscreening agents, antioxidants, fillers, electrolytes, colorants, inorganic or organic customary bases or acids, perfumes, essential oils, cosmetic active agents, moisturizers, vitamins, essential fatty acids, sphingolipids, self-tanning compounds such as DHA, soothing agents and agents for protecting the skin such as allantoin, propenetrating agents, or optionally a mixture thereof, a benzoyl peroxide stabilizer (by way of example sodium docusate, sodium C14-16 olefin sulfonate). Of course, one skilled in the art will take care to select this or these optional additional compounds, and/or their quantity, such that the advantageous properties of the compositions according to the invention are not, or not substantially, impaired.

These additives may be present in the composition in an amount of 0.001% to 20% by weight relative to the total weight of the composition.

In one particular embodiment of the invention, the composition is provided in the form of an oil-in-water (O/W) emulsion of the lotion, cream or gel cream type and comprises:
  from 0.1% to 0.3% of a naphthoic acid compound;
  from 1% to 10% of benzoyl peroxide;
  from 1% to 10% of one or more polymers of polyurethane or derivatives;
  from 0.1% to 7%, in a particular embodiment from 0.1% to 3% of one or more gelling agents or suspending agents;
  from 0% to preferably from 0.01 to 1.5% of one or more chelating agents;
  from 0.1% to 10% of one or more wetting agents; from 0.1% to 20% of an emollient agent;
  from 0.1% to 30% of fatty phase;
  from 0% to 3%, in a particular embodiment from 0.01% to 3% of preservatives;
  from 0% to 10% of emulsifiers;
  from 0 to 2% of stabilizing agents.

In another particular embodiment of the invention, the composition is provided in gel form and comprises:
  from 0.1% to 0.3% of a naphthoic acid compound;
  from 1% to 10% of benzoyl peroxide;
  from 1% to 10% of one or more polymers of polyurethane or derivatives;
  from 0.1% to 7%, in a particular embodiment from 0.1% to 3% of one or more gelling agents or suspending agents;
  from 0% to preferably from 0.01 to 1.5% of one or more chelating agents;
  from 1% to 10% of one or more wetting agents; from 1% to 20% of an emollient agent;

from 0% to 3%, in a particular embodiment from 0.01% to 3% of preservatives;
from 0% to 2% of stabilizing agents.

In another particular embodiment of the invention, the composition is provided in gel cream form and comprises:
from 0.1% to 0.3% of a naphthoic acid compound;
from 1% to 10% of benzoyl peroxide;
from 1% to 10% of one or more polymers of polyurethane or derivatives;
from 0.1% to 7%, in a particular embodiment from 0.1% to 3% of one or more gelling agents or suspending agents;
from 0% to 1.5% of one or more chelating agents;
from 1% to 10% of one or more wetting agents;
from 0.1% to 20% of an emollient agent;
from 0.1 to 30% of fatty phase;
from 0.01% to 3% of preservatives;
from 0% to 2% of stabilizing agents.

In a particular embodiment of the invention, the composition is provided in lotion form and comprises:
from 0.1% to 0.3% of a naphthoic acid compound;
from 1% to 10% of benzoyl peroxide;
from 1% to 10% of one or more polymers of polyurethane or derivatives;
from 0.1% to 7%, in a particular embodiment from 0.1% to 3% of one or more gelling agents or suspending agents;
from 0% to 1.5% of one or more chelating agents;
from 1% to 10% of one or more wetting agents;
from 0.1% to 20% of an emollient agent;
from 0.1% to 30% of fatty phase;
from 0.01% to 3% of preservatives;
from 0% to 10% of emulsifiers;
from 0% to 2% of stabilizing agents.

In a particular embodiment of the invention, the composition is provided in cream form and comprises:
from 0.1% to 0.3% of a naphthoic acid compound;
from 1% to 10% of benzoyl peroxide;
from 1% to 10% of one or more polymers of polyurethane or derivatives;
from 0.1% to 7%, in a particular embodiment from 0.1% to 3% of one or more gelling agents or suspending agents;
from 0.01% to 1.5% of one or more chelating agents;
from 1% to 10% of one or more wetting agents;
from 0.1% to 20% of an emollient agent;
from 0.1% to 30% of fatty phase;
from 0.01% to 3% of preservatives;
from 0% to 10% of emulsifiers;
from 0% to 2% of stabilizing agents.

The present invention also features a method for preparing a composition as described above. Such a method is characterized in that it comprises the step of mixing a physiologically acceptable vehicle comprising at least one naphthoic acid compound with benzoyl peroxide and with at least one compound of the polyurethane polymer type or derivatives thereof, the said derivative of naphthoic acid and benzoyl peroxide being in dispersed form in the said composition.

The introduction of other optional excipients and additives will be carried out according to the chemical nature of the compounds and of the galenic form selected.

The formulation of a composition according to the invention is carried out in 3 or 5 steps according to the galenic form selected, the additional two steps being carried out only for the preparation of emulsion type forms such as creams, lotions, gel creams.

The introduction of the polyolprepolymer in one or other of the steps depends on the lipophilic or hydrophilic nature of the polyolprepolymer. Thus, the PP-2 type polyolprepolymer which is of a lipophilic nature is introduced into the fatty phase for the emulsions and after the neutralization step for the gels. The PP-15 type polyolprepolymer, which is hydrophilic, is introduced into the active aqueous phase.

The formulation of a composition according to the invention is thus carried out according to the following main method:

a) The naphthoic acid compound is mixed with at least one wetting agent, in water, until the said naphthoic acid compound is perfectly dispersed, to obtain the active phase 1;

b) The benzoyl peroxide is mixed with at least one wetting agent, in water, until the said benzoyl peroxide is perfectly dispersed, to obtain the active phase 2;

c) One or more gelling agents (with the exception of polyacrylamide), optionally, a chelating agent, one or more preservatives, one or more emollients, one or more emulsifiers, a suspending agent and a stabilizing agent are solubilized in water, if necessary in the hot state. The stirring and optional heating are maintained until homogeneity is obtained, to obtain the aqueous phase;

d) Optionally, to obtain an emulsion, at least lipophilic emulsifiers, oils and/or solid fatty substances are mixed with preservatives, to obtain the fatty phase;

e) The two active phases obtained respectively in a) and b) are mixed. A single active phase is obtained;

f) Optionally, the said fatty phase obtained in d) is introduced into the aqueous phase obtained in c) to obtain an emulsion;

g) The single active phase obtained in e) is added to the phase obtained in f) for the emulsions and to the phase obtained in c) for the gels and gel creams;

h) Optionally, the polyacrylamide is introduced, with stirring, into the phase obtained in g). The stirring is maintained until perfect homogeneity is obtained;

i) Optionally, for gel creams, the oil is introduced, with stirring, into the mixture obtained in step g) or h);

j) If necessary, an agent for neutralizing the gelling agent is introduced. In the case of an emulsion, it will be introduced into the phase obtained in step g). In the case of a gel, it will be introduced into the phase obtained in step g) or h). In the case of a gel cream, it will be introduced into the phase obtained in i). The compound of the polyurethane polymer type or derivatives thereof are introduced into the aqueous active phase obtained in a) or b) or into the fatty phase obtained in step d) or after step j) according to its lipophilic or hydrophilic nature.

The formulation of a composition according to the invention is thus carried out according to the following alternative method:

the active ingredients are mixed in the 1st step of the method described above; steps a) and b) are thus replaced by step a'):

a') the naphthoic acid compound and the benzoyl peroxide are mixed with at least one wetting agent, in water, until the said benzoyl peroxide and the said naphthoic acid compound are perfectly dispersed to obtain a single active phase.

The method is then continued as described from step c).

More precisely, the main method for formulating the composition according to the invention comprises the following steps:

Step a: Preparation of the Active Phase 1:

Purified water, the active ingredient (adapalene) and the wetting agents (such as Synperonic PE/L62, Synperonic PE/L44, propylene glycol) are introduced, with stirring, into a beaker. The mixture is kept stirred until a perfect dispersion is obtained.

Step b: Preparation of the Active Phase 2:

Purified water, the active ingredient (benzoyl peroxide) and the wetting agents (such as Synperonic PE/L62, Synperonic PE/L44, propylene glycol) are introduced, with stirring, into a beaker. The mixture is kept stirred until a perfect dispersion is obtained.

Step c: Preparation of the Aqueous Phase:

Purified water and the gelling agent(s) (with the exception of Simulgel 600PHA), optionally, the chelating agent (EDTA type), the emollients (glycerine type), the preservative (methylparaben type), the emulsifiers, the suspending agent (Avicel type) and the stabilizing agent (sodium docusate type) are introduced, with stirring, if necessary in the hot state, into a beaker.

Step d: (Optional): Preparation of the Fatty Phase:

The emulsifiers (such as Glucate SS, Glucamate SSE 20, Brij 721, Tefose, Arlacel 165FL, Tween 80), the oily compounds (such as isostearic olepal, Cetiol SN, Crodamol DA, Speziol C18, Miglyol 812, Cosbiol, Marcol 152, ST-Cyclomethicone 5NF) and the preservatives (such as phenoxyethanol and propylparaben) are introduced, with stirring, into an auxiliary beaker. The mixture is heated until homogenization is obtained and the volatile silicone is introduced if the latter is present in the composition.

Step e: Mixing of the Active Phases:

At a temperature below 40° C., the two active phases obtained respectively in a) and b) are mixed, the stirring being maintained until perfect homogenization is obtained.

Step f (Optional): Emulsification:

At the temperature of 60° C. and with stirring, the fatty phase is gently introduced into the aqueous phase to carry out the emulsification. The heating is maintained for 5 minutes, and then the product is allowed to cool slowly. The stirring is adjusted according to the viscosity.

Steps d) and f) are optional and are only carried out for the preparation of emulsion type forms such as creams and lotions.

Step g:

Introduction of the sole active phase obtained in e) into the aqueous phase obtained in c) for the gels and gel creams or into the phase obtained in 0 for the emulsions.

Step h (Optional): Addition of Simulgel 600Pha:

Simulgel 600PHA is introduced, with stirring, into the phase obtained in g). The stirring is maintained until perfect homogeneity is obtained.

Step i (Optional): Addition of the Oil for the Gel Creams:

The oil is added to the mixture obtained in step g) or h), with stirring.

Step j: Neutralization:

At a temperature below 40° C., if necessary, the agent for neutralizing the gelling agent (such as triethanolamine, 10% sodium hydroxide solution, citric acid/sodium citrate buffer, succinic acid/sodium succinate buffer) is introduced if necessary, up to a pH of 5.5+/−0.5. The product then takes on a thicker consistency. At the end of the manufacture, the pH is again checked. If necessary, the adjustment of the water is carried out. The product is homogenized for one last time to ensure good dispersion of the active ingredient Adapalene (microscopic observation showing a homogeneous dispersion having no aggregates), and then the product is packaged.

The compound of the polyurethane polymer type is preferably a polyolprepolymer which is introduced during steps a) or b) (for gel or gel cream or emulsion formulations comprising a hydrophilic polymer) or during step d) (for emulsion formulations comprising a lipophilic polymer) or after step j) (for gel formulations comprising a lipophilic polymer) according to its lipophilic or hydrophilic nature.

More precisely, the alternative method for preparing the composition according to the invention comprises the following steps:

Step a Preparation of the Single Active Phase:

Purified water, the active ingredients (adapalene and benzoyl peroxide) and the wetting agents (such as Synperonic PE/L62, Synperonic PE/L44, propylene glycol) are introduced, with stirring, into a beaker. The mixture is kept stirred until a perfect dispersion is obtained.

Step b Preparation of the Aqueous Phase:

Purified water and the gelling agent(s) (with the exception of Simulgel 600PHA), optionally, the chelating agent (EDTA type), the emollients (glycerine type), the emulsifiers, the preservative (methylparaben type), the suspending agent (Avicel type) and the stabilizing agent (sodium docusate type) are introduced, with stirring, if necessary in the hot state, into a beaker.

Step c (Optional): Preparation of the Fatty Phase:

The emulsifiers (such as Glucate SS, Glucamate SSE 20, Brij 721, Tefose, Arlacel 165FL, Tween 80), the oily compounds (such as isostearic olepal, Cetiol SN, Crodamol DA, Speziol C18, Miglyol 812, Cosbiol, Marcol 152, ST-Cyclomethicone 5NF) and the preservatives (such as phenoxyethanol and propylparaben) are introduced, with stirring, into an auxiliary beaker. The mixture is heated until homogenization is obtained and the volatile silicone is introduced if the latter is present in the composition.

Step d (Optional): Emulsification:

At the temperature of 60° C. and with stirring, the fatty phase is gently introduced into the aqueous phase to carry out the emulsification. The heating is maintained for from 3 and 8 minutes, and then the product is allowed to cool. The stirring is adjusted according to the viscosity.

Steps c) and d) are optional and are only carried out for the preparation of emulsion type forms such as creams and lotions.

Step e:

Introduction of the sole active phase obtained in a) into the aqueous phase obtained in b) (for the gels and gel creams) or into the phase obtained in d) (for the emulsions).

Step f (Optional): Addition of Simulgel 600PHA:

Simulgel 600PHA is introduced, with stirring, into the phase obtained in e). The stirring is maintained until perfect homogeneity is obtained.

Step g (Optional): Addition of the Oil for the Gel Creams:

The oil is added to the mixture obtained in step e) or f), with stirring.

Step h: Neutralization:

At a temperature below 40° C., the agent for neutralizing the gelling agent (such as triethanolamine, 10% sodium hydroxide solution, citric acid/sodium citrate buffer, succinic acid/sodium succinate buffer) is introduced if necessary, up to a pH of 5.5+/−0.5. The product then takes on a thicker consistency. At the end of the manufacture, the pH is again checked. If necessary, the adjustment of the water is carried out. The product is homogenized for one last time to ensure good dispersion of the active ingredient Adapalene (microscopic observation showing a homogeneous dispersion having no aggregates), and then the product is packaged.

The compound of the polyurethane polymer type is preferably a polyolprepolymer which is introduced during step a) (for gel or gel cream or emulsion formulations comprising a hydrophilic polymer) or during step c) (for emulsion formulations comprising a lipophilic polymer) or after step h) (for gel formulations comprising a lipophilic polymer) according to its lipophilic or hydrophilic nature.

The present invention also features administration of the compositions as described above, as medicaments, in a regimen/regimen.

The invention also features application of the novel compositions as described above in cosmetics and in dermatology.

In particular, this invention features formulation of a composition as described above into pharmaceutical compositions useful for the treatment and/or prevention of dermatological conditions/afflictions linked to a keratinization disorder relating to cell differentiation and proliferation, and in particular for treating acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, acne rosacea, senile acne, solar acne and acne medicamentosa.

More particularly, this invention features formulation of compositions as described above into pharmaceutical composition useful for the prevention or treatment of acne vulgaris.

Preferably, the said compositions according to the invention are administered topically.

In addition, the present invention also features the cosmetic application of a subject composition for the treatment of skin which is prone to acne, for combating the greasy appearance of the skin or the hair, in the protection against the harmful effects of the sun or in the treatment of physiologically greasy skin.

In order to further illustrate the present invention and the advantages thereof, the following specific examples are given, it being understood that same are intended only as illustrative and in nowise limitative. In said examples to follow, all parts and percentages are given by weight, unless otherwise indicated.

The expression study of the physical stability of the formulations means the carrying out of a macroscopic and microscopic examination at room temperature, 40° C. performed at T1 month, T2 months and optionally T+15 days.

The microscopic examination makes it possible to evaluate the quality of the dispersion of the two active agents. Adapalene is examined in fluorescent light while benzoyl peroxide is examined in polarized light.

The characterization of the finished product is supplemented by a measurement of the yield point and the viscosity.

For the measurement of the yield point, a HAAKE VT550 type rheometer with an SVDIN measuring rotor is used.

The rheograms are produced at 25° C., at the shear rate of 4 s$^{-1}$, 20 s$^{-1}$ and 100 s$^{-1}$ ($\gamma$) and by measuring the shear stress. The expression yield point ($\tau$0 expressed in Pascal) means the force required (minimum shear stress) to overcome the Van der Waals type forces of cohesion and cause flow. The yield point is comparable to the value found at the shear rate of 4 s$^{-1}$.

To measure the viscosity, the Brookfield RVDVII+ or LVDVII+ viscometers are used. The viscosity ranges which can be measured with the 2 types of Brookfield are the following:

RVDVII+: 100 cP-40 McP
LVDVII+: 15 cP-6 McP

It will be considered that the following exists at the initial time T0:
a cream or a gel cream if the viscosity is greater than 30,000 cP at the initial time T0;
a lotion if the viscosity is less than 30,000 cP at the initial time T0 (Lucinda Bushe, ACPS 22 Oct. 2003 Pharmaceutical nomenclature-Issues and challenges).

The chemical stability is obtained by an HPLC assay of the active agents.

The result is expressed in mg/g of adapalene and benzoyl peroxide and in % in relation to the expected titre.

Example 1

Formulation of the Gel Type Containing 2.5% Benzoyl Peroxide, 0.1% Adapalene and the Polyolprepolymer-2

The composition is prepared according to the procedure described above:

Constituents Content (% m/m):

| | |
|---|---|
| Benzoyl peroxide | 2.50% |
| Adapalene | 0.10% |
| Propylene glycol | 4.00% |
| Synperonic PE/L44 | 0.20% |
| EDTA | 0.10% |
| Glycerine | 4.00% |
| Polyolprepolymer-2 | 1.00% |
| Sodium docusate | 0.05% |
| Simulgel 600PHA | 4.00% |
| Purified water | qs 100% |

Physical Stability:

| Characterizations at T0 | |
|---|---|
| Macroscopic appearance | White gel |
| Microscopic appearance | Good dispersion of the 2 active agents. |
| | ADAPALENE |
| | 90% < 20 μm |
| | 99% < 50 μm |
| | BENZOYL PEROXIDE |
| | 95% < 25 μm |
| | 99% < 100 μm |
| pH | 3.668 |
| Viscosity data Haake (4 s-1/20 s-1/100 s-1) | 118/162/290 |

| | | T1 month | T6 weeks | T2 months |
|---|---|---|---|---|
| Macroscopic appearance | RT | Identical to T0 | Identical to T0 | Identical to T0 |
| | 40° C. | Identical to T0 | Identical to T0 | Identical to T0 |
| Microscopic appearance | RT | Identical to T0 | Identical to T0 | Identical to T0 |
| | 40° C. | Identical to T0 | Identical to T0 | Identical to T0 |
| pH | RT | 3.71 | 3.78 | 3.82 |
| | 40° C. | 3.56 | 3.51 | 3.54 |
| Haake rheology 4 s-1/20 s-1/100 s-1 | | 127/178/275 | 97/137/233 | 127/182/279 |

Chemical Stability:
♭ Adapalene:

| Stability | | Time | |
|---|---|---|---|
| conditions | | T0 | T1 month |
| RT | g/g | 0.0953 | 0.0979 |
| | % expected titre | 95 | 98 |
| 40° C. | g/g | NA | 0.0991 |
| | % expected titre | NA | 99 |

✥ Benzoyl Peroxide:

| Stability conditions | | Time | |
|---|---|---|---|
| | | T 0 | T1 month |
| RT | g/g | 2.5081 | 2.4727 |
| | % expected titre | 100.3 | 99 |
| 40° C. | g/g | NA | 2.3922 |
| | % expected titre | NA | 96 |

Example 2

Formulation of the Gel Type Containing 2.5% Benzoyl Peroxide, 0.1% Adapalene and Polyolprepolymer-15

The composition is prepared according to the procedure described above:

Constituents Content (% m/m):

| Benzoyl peroxide | 2.50 |
|---|---|
| Adapalene | 0.10 |
| Propylene glycol | 4.00 |
| Synperonic PE/L44 | 0.20 |
| EDTA | 0.10 |
| Glycerine | 4.00 |
| Polyolprepolymer-15 | 1.00 |
| Sodium docusate | 0.05 |
| Simulgel 600PHA | 4.00 |
| Purified water | qs 100% |

Stability Data:

Physical Stability:

| Characterizations at T0 | |
|---|---|
| Macroscopic appearance | White gel |
| Microscopic appearance | Good dispersion of the 2 active agents |
| | ADAPALENE |
| | 90% < 20 μm |
| | 99% < 50 μm |
| | BENZOYL PEROXIDE |
| | 95% < 25 μm |
| | 99% < 100 μm |
| pH | 3.701 |
| Viscosity data  Haake (4 s-1/20 s-1/100 s-1) | 93/112/178 |

| | | T1 month | T6 weeks | T2 months |
|---|---|---|---|---|
| Macroscopic appearance | RT | Identical to T0 | Identical to T0 | Identical to T0 |
| | 40° C. | Identical to T0 | Identical to T0 | Identical to T0 |
| Microscopic appearance | RT | Identical to T0 | Identical to T0 | Identical to T0 |
| | 40° C. | Identical to T0 | Identical to T0 | Identical to T0 |
| pH | RT | 3.80 | 3.80 | 3.71 |
| | 40° C. | 3.65 | 3.65 | 3.64 |
| Haake rheology 4 s-1/20 s-1/100 s-1 | | 97/132/221 | 103/132/231 | 100/141/223 |

Chemical Stability:

✥ Adapalene:

| Stability conditions | | Time | | |
|---|---|---|---|---|
| | | T0 | T1 month | T6 weeks |
| RT | g/g | 0.0982 | 0.10157 | 0.1040 |
| | % expected titre | 98 | 102 | 104 |
| 40° C. | g/g | NA | 0.10203 | 0.1074 |
| | % expected titre | NA | 102 | 107 |

✥ Benzoyl Peroxide:

| Stability conditions | | Time | | |
|---|---|---|---|---|
| | | T0 | T1 month | T6 weeks |
| RT | g/g | 2.5747 | 2.5081 | 2.3602 |
| | % expected titre | 103 | 100 | 94 |
| 40° C. | g/g | NA | 2.4772 | 2.3474 |
| | % expected titre | NA | 99 | 94 |

Example 3

Formulation of the Gel Type Containing 0.1% Adapalene and 2.5% Benzoyl Peroxide and Polyolprepolymer-15:

Constituents Content (% m/m):

| Benzoyl peroxide | 2.50 |
|---|---|
| Adapalene | 0.10 |
| Propylene glycol | 4.00 |
| Synperonic PE/L44 | 0.20 |
| EDTA | 0.10 |
| Glycerine | 4.00 |
| Polyolprepolymer-15 | 5.00 |
| Sodium docusate | 0.05 |
| Simulgel 600PHA | 4.00 |
| Purified water | qs 100% |

Stability Data:

Physical Stability:

| Characterizations at T0 | |
|---|---|
| Macroscopic appearance | White gel |
| Microscopic appearance | Good dispersion of the 2 active agents. |
| | ADAPALENE |
| | 90% < 20 μm |
| | 99% < 50 μm |
| | BENZOYL PEROXIDE |
| | 95% < 25 μm |
| | 99% < 100 μm |
| pH | 3.748 |
| Viscosity data  Haake (4 s-1/20 s-1/100 s-1) | 93/138/234 |

-continued

| Characterizations at T0 | | | | |
|---|---|---|---|---|
| | | T1 month | T6 weeks | T + 2 months |
| Macroscopic appearance | RT | Identical to T0 | Identical to T0 | Identical to T0 |
| | 40° C. | Identical to T0 | Identical to T0 | Identical to T0 |
| Microscopic appearance | RT | Identical to T0 | Identical to T0 | Identical to T0 |
| | 40° C. | Identical to T0 | Identical to T0 | Identical to T0 |
| pH | RT | 3.78 | 3.70 | 3.74 |
| | 40° C. | 3.71 | 3.51 | 3.69 |
| Haake rheology 4 s-1/20 s-1/100 s-1 | | 94/139/227 | 95/147/231 | 87/135/247 |

Chemical Stability:

✤ Adapalene:

| Stability | | Time | |
|---|---|---|---|
| conditions | | T0 | T1 month |
| RT | g/g | 0.0873 | 0.1004 |
| | % expected titre | 87 | 100 |
| 40° C. | g/g | NA | 0.0989 |
| | % expected titre | NA | 99 |

✤ Benzoyl Peroxide:

| Stability | | Time | |
|---|---|---|---|
| conditions | | T0 | T1 month |
| RT | g/g | 2.5198 | 2.4394 |
| | % expected titre | 101 | 98 |
| 40° C. | g/g | NA | 2.322 |
| | % expected titre | NA | 93 |

Example 4

Formulation of the Cream Type Containing 0.1% Adapalene and 2.5% Benzoyl Peroxide and Polyolprepolymer-2:

The composition is prepared according to the procedure described above:

Constituents Content (% m/m):

| | |
|---|---|
| Benzoyl peroxide | 2.50 |
| Adapalene | 0.10 |
| Propylene glycol | 4.00 |
| Synperonic PE/L44 | 0.20 |
| Sodium docusate | 0.05 |
| Propylene glycol | 2.00 |
| EDTA | 0.10 |
| Carbopol Ultrez 20 | 0.40 |
| Glycerine | 3.00 |
| Glucamate SSE 20 | 3.50 |
| Glucate SS | 3.50 |
| Perhydrosqualene | 6.00 |
| ST-Cyclomethicone 5 NF | 13.00 |
| Polyolprepolymer-2 | 1.00 |
| Purified water | qs 100% |
| Triethanolamine | qs pH 5.5 ± 0.5 |

Stability Data:

| Characterizations at T0 | | |
|---|---|---|
| Macroscopic appearance | | White cream |
| Microscopic appearance | | Good dispersion of the 2 active agents. |
| | | ADAPALENE |
| | | 90% < 20 µm |
| | | 99% < 50 µm |
| | | BENZOYL PEROXIDE |
| | | 95% < 25 µm |
| | | 99% < 100 µm |
| pH | | 5.99 |
| Viscosity data | Haake (4 s-1/20 s-1/100 s-1) | 306/443/568 |
| | Brookfield RVDVII+ (S29; 5 rpm) | >200000 cP |

Chemical Stability:

| | | T1 month | T2 months |
|---|---|---|---|
| Macroscopic appearance | RT | Identical to T0 | Identical to T0 |
| | 40° C. | Identical to T0 | Identical to T0 |
| Microscopic appearance | RT | Identical to T0 | Identical to T0 |
| | 40° C. | Identical to T0 | Identical to T0 |
| pH | RT | 5.95 | 5.81 |
| | 40° C. | 5.30 | 4.44 |
| Viscosity data | Haake (4 s-1/20 s-1/100 s-1) | 271/383/336 | NA |
| | Brookfield RVDVII+ (S29; 5 rpm) | 189 940 cP | >200000 cP |

✤ Adapalene:

| Stability | | Time | |
|---|---|---|---|
| conditions | | T0 | T1 M |
| RT | g/g | 0.10 | 0.10 |
| | % expected titre | 100 | 100 |
| 40° C. | g/g | NAN. | 0.10 |
| | % expected titre | | 100 |

✤ Benzoyl Peroxide:

| Stability | | Time | |
|---|---|---|---|
| conditions | | T0 | T1 M |
| RT | g/g | 2.60 | 2.60 |
| | % expected titre | 104 | 104 |
| 40° C. | g/g | N.A. | 2.30 |
| | % expected titre | | 92 |

Example 5

Formulation of the Cream Type Containing 0.3% Adapalene and 5% Benzoyl Peroxide and Polyolprepolymer-2L The composition is prepared according to the procedure described above:

Constituents Content (% m/m):

| | |
|---|---|
| Benzoyl peroxide | 5.00 |
| Adapalene | 0.30 |
| Dipropylene glycol | 5.00 |
| Synperonic PE/L44 | 0.20 |
| Glycerine | 7.00 |
| Xantural 180 | 0.4 |
| Eumulgin B2 PH | 3.00 |
| Arlacel 165FL | 3.00 |
| Speziol C18 Pharma | 2.00 |
| Miglyol 812 N | 7.00 |
| ST-Cyclomethicone 5 NF | 6.00 |
| Simulgel 600 PHA | 2.50 |
| Polyolprepolymer-2 | 3.00 |
| Purified water | qs 100 |
| Sodium hydroxide | qs pH 5.5 ± 0.5 |

Stability Data:

Physical Stability:

| Characterizations at T0 | |
|---|---|
| Macroscopic appearance | White cream |
| Microscopic appearance | Good dispersion of the 2 active agents. |
| | ADAPALENE |
| | 90% < 20 μm |
| | 99% < 50 μm |
| | BENZOYL PEROXIDE |
| | 95% < 25 μm |
| | 99% < 100 μm |
| pH | 6.45 |
| Viscosity data  Haake (4 s-1/20 s-1/100 s-1) | 107/168/265 |
| Brookfield RVDVII+ (S29; 5 rpm) | 98 640 cP |

| | | T1 month | T2 months |
|---|---|---|---|
| Macroscopic appearance | RT | Identical to T0 | Identical to T0 |
| | 40° C. | Identical to T0 | Identical to T0 |
| Microscopic appearance | RT | Identical to T0 | Identical to T0 |
| | 40° C. | Identical to T0 | Identical to T0 |
| pH | RT | 5.56 | 5.18 |
| | 40° C. | 3.98 | 3.72 |
| Viscosity data | Haake (4 s-1/20 s-1/100 s-1) | 124/198/257 | 117/175/244 |
| | Brookfield RVDVII+ (S29; 5 rpm) | 93 180 cP | 97840 cP |

Chemical Stability:

✎ Adapalene:

| Stability | | Time | |
|---|---|---|---|
| conditions | | T0 | T1 M |
| RT | g/g | 0.28 | 0.28 |
| | % expected titre | 93.33 | 93.33 |
| 40° C. | g/g | N.A. | 0.28 |
| | % expected titre | N.A. | 93.33 |

✎ Benzoyl Peroxide:

| Stability | | Time | |
|---|---|---|---|
| conditions | | T0 | T1 M |
| RT | g/g | 5.20 | 5.10 |
| | % expected titre | 104 | 102 |
| 40° C. | g/g | N.A. | 4.30 |
| | % expected titre | | 86 |

Example 6

Formulation of the Lotion Type Containing 0.3% Adapalene and 1% Benzoyl Peroxide and Polyolprepolymer-2

The composition is prepared according to the procedure described above:

Constituents Content (% m/m):

| | |
|---|---|
| Benzoyl peroxide | 1.00 |
| Adapalene | 0.30 |
| Dipropylene glycol | 3.00 |
| Synperonic PE/L44 | 0.20 |
| Methylparaben | 0.15 |
| Avicel CL-611 | 1.50 |
| Brij 721 | 3.00 |
| Arlacel 165FL | 3.00 |
| Propylparaben | 0.05 |
| Perhydrosqualene | 5.00 |
| Cetiol SN PH | 5.00 |
| Simulgel 600 PHA | 1.50 |
| Polyolprepolymer-2 | 1.00 |
| Purified water | qs 100% |
| Triethanolamine | qs pH 5.5 ± 0.5 |

Stability Data:
Physical Stability:

| Characterizations at T0 | |
|---|---|
| Macroscopic appearance | White lotion |
| Microscopic appearance | Good dispersion of the 2 active agents. |
| | ADAPALENE |
| | 90% < 20 μm |
| | 99% < 50 μm |
| | BENZOYL PEROXIDE |
| | 95% < 25 μm |
| | 99% < 100 μm |

-continued

| Characterizations at T0 | | |
|---|---|---|
| pH | | 5.868 |
| Viscosity data | Haake (4 s-1/20 s-1/100 s-1) | 24/41/87 |
| | Brookfield LVDVII+ (S63; 5 rpm) | 21211 cP |

| | | T15 days | T1 month |
|---|---|---|---|
| Macroscopic appearance | RT | Identical to T0 | Identical to T0 |
| | 40° C. | Identical to T0 | Identical to T0 |
| Microscopic appearance | RT | Identical to T0 | Identical to T0 |
| | 40° C. | Identical to T0 | Identical to T0 |
| pH | RT | 5.42 | 5.13 |
| | 40° C. | 4.34 | 3.96 |
| Haake rheology 4 s-1/20 s-/100 s-1 | | 21/36/74 | 18/33/70 |
| Viscosity Brookfield LVDVII+ (S63; 5 rpm) | | 16916 cP | 15453 cP |

Chemical Stability:

✧ Adapalene:

| Stability | | Time | |
|---|---|---|---|
| conditions | | T0 | T15 days |
| RT | g/g | 0.29 | 0.29 |
| | % expected titre | 97 | 97 |
| 40° C. | g/g | NA | 0.29 |
| | % expected titre | NA | 97 |

✧ Benzoyl Peroxide:

| Stability | | Time | |
|---|---|---|---|
| conditions | | T0 | T15 days |
| RT | g/g | 1.2 | 1.2 |
| | % expected titre | 120 | 120 |
| 40° C. | g/g | NA | 1.1 |
| | % expected titre | NA | 110 |

Example 7

Formulation of the Gel Cream Type Containing 0.1% Adapalene and 2.5% Benzoyl Peroxide and Polyolprepolymer-15:

The composition is prepared according to the procedure described above:

Constituents Content (% m/m):

| | |
|---|---|
| Benzoyl peroxide | 2.50 |
| Adapalene | 0.10 |
| Propylene glycol | 5.00 |
| Synperonic PE/L44 | 0.20 |
| EDTA | 0.10 |
| Glycerine | 5.00 |
| Xantural 180 | 0.10 |
| Carbopol Ultrez 20 | 0.70 |
| Marcol 152 | 7.00 |
| Polyolprepolymer-15 | 1.00 |
| Purified water | qs 100 |
| Sodium hydroxide 10% m/m | qs pH 5.5 ± 0.5 |

Stability Data:

Physical Stability:

| Characterizations at T0 | | |
|---|---|---|
| Macroscopic appearance | | White gel cream |
| Microscopic appearance | | Good dispersion of the 2 active agents. |
| | | ADAPALENE |
| | | 90% < 20 μm |
| | | 99% < 50 μm |
| | | BENZOYL PEROXIDE |
| | | 95% < 25 μm |
| | | 99% < 100 μm |
| pH | | 5.169 |
| Viscosity data | Haake (4 s-1/20 s-1/100 s-1) | 54/89/150 |
| | Brookfield RVDVII+ (S27; 5 rpm) | 31634 cP |

| | | T1 month | T2 months |
|---|---|---|---|
| Macroscopic appearance | RT | Identical to T0 | Identical to T0 |
| | 40° C. | Identical to T0 | Identical to T0 |
| Microscopic appearance | RT | Identical to T0 | Identical to T0 |
| | 40° C. | Identical to T0 | Identical to T0 |
| pH | RT | 5.10 | 5.07 |
| | 40° C. | 4.98 | 4.79 |
| Haake rheology 4 s-1/20 s-1/100 s-1 | | 50/83/147 | 49/81/142 |
| Brookfield viscosity RVDVII+ (S27; 5 rpm) | | 28535 cP | 30780 cP |

Chemical Stability:

✧ Adapalene:

| Stability | | Time | |
|---|---|---|---|
| conditions | | T0 | T1 month |
| RT | g/g | 0.10 | 0.10 |
| | % expected titre | 100 | 100 |
| 40° C. | g/g | NA | 0.10 |
| | % expected titre | NA | 100 |

✧ Benzoyl Peroxide:

| Stability | | Time | |
|---|---|---|---|
| conditions | | T0 | T1 month |
| RT | g/g | 2.8 | 2.7 |
| | % expected titre | 112 | 108 |
| 40° C. | g/g | NA | 2.6 |
| | % expected titre | NA | 104 |

Example 8

Formulation of the Thick Gel Cream Type Containing 0.10% Adapalene and 2.5% Benzoyl Peroxide and Polyolprepolymer-2

The composition is prepared according to the procedure described below:

Constituents Content (% m/m):

| | |
|---|---|
| Benzoyl peroxide | 2.50 |
| Adapalene | 0.10 |
| Propylene glycol | 6.00 |
| Synperonic PE/L44 | 0.20 |
| Glycerine | 5.00 |
| ST-Cyclomethicone 5NF | 7.00 |
| Simulgel 600 PHA | 4.00 |
| Polyolprepolymer-2 | 1.00 |
| Purified water | qs 100 |

Stability Data:

Physical Stability:

| Characterizations at T0 | | |
|---|---|---|
| Macroscopic appearance | | White gel cream |
| Microscopic appearance | | Good dispersion of the 2 active agents. |
| | | ADAPALENE |
| | | 90% < 20 µm |
| | | 99% < 50 µm |
| | | BENZOYL PEROXIDE |
| | | 95% < 25 µm |
| | | 99% < 100 µm |
| pH | | 3.622 |
| Viscosity data | Haake (4 s-1/20 s-1/100 s-1) | 209/277/423 |
| | Brookfield RVDVII+ (S29; 5 rpm) | 131320 cP |

| | | T1 month | T2 months |
|---|---|---|---|
| Macroscopic appearance | RT | Identical to T0 | Identical to T0 |
| | 40° C. | Identical to T0 | Identical to T0 |
| Microscopic appearance | RT | Identical to T0 | Identical to T0 |
| | 40° C. | Identical to T0 | Identical to T0 |
| pH | RT | 3.45 | 3.42 |
| | 40° C. | 3.32 | 3.23 |
| Haake rheology 4 s-1/20 s-1/100 s-1 | | 202/291/318 | 200/278/408 |
| Brookfield viscosity RVDVII+ (S29; 5 rpm) | | 144280 cP | 144720 cP |

Chemical Stability:

✤ Adapalene:

| Stability | | Time | |
|---|---|---|---|
| conditions | | T0 | T1 month |
| RT | g/g | 0.10 | 0.10 |
| | % expected titre | 100 | 100 |
| 40° C. | g/g | NA | 0.10 |
| | % expected titre | NA | 100 |

✤ Benzoyl Peroxide:

| Stability | | Time | |
|---|---|---|---|
| conditions | | T0 | T1 month |
| RT | g/g | 2.7 | 2.7 |
| | % expected titre | 108 | 108 |
| 40° C. | g/g | NA | 2.3 |
| | % expected titre | NA | 92 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable dermatological/pharmaceutical composition comprising (i) benzoyl peroxide, (ii) at least one naphthoic acid compound, and (iii) at least one polyurethane polymer; said at least one naphthoic acid compound and said benzoyl peroxide being dispersed in said composition; said benzoyl peroxide and said at least one naphthoic acid compound being present in anti-acne effective amounts and being the only anti-acne active agents in said composition; said (i), (ii) and (iii) being formulated into a physiologically acceptable medium as a cream, lotion or gel cream comprising a fatty phase.

2. The dermatological/pharmaceutical composition as defined by claim 1, said at least one naphthoic acid compound having the formula (I):

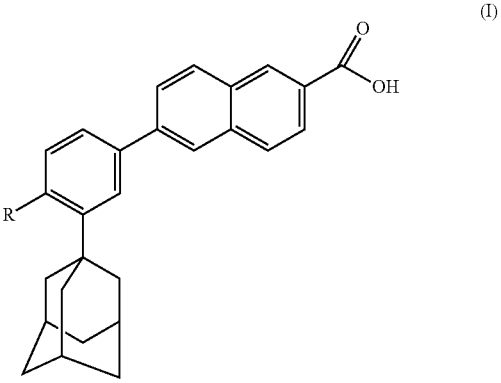

in which:
R is a hydrogen atom, a hydroxyl radical, a branched or unbranched alkyl radical having from 1 to 4 carbon atoms, an alkoxy radical having from 1 to 10 carbon atoms or a cycloaliphatic radical.

3. The dermatological/pharmaceutical composition as defined by claim 1, wherein the concentration of the at least one naphthoic acid compound ranges from 0.001% to 10% by weight of the total weight of the composition.

4. The dermatological/pharmaceutical composition as defined by claim 1, said at least one naphthoic acid compound being selected from the group consisting of 6-[3-(1-adamantyl)-4-methoxyphenyl]-2-naphthoic acid, 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid.

5. The dermatological/pharmaceutical composition as defined by claim 1, said at least one naphthoic acid compound being 6-[3-(1-adamantyl)-4-methoxyphenyl]-2-naphthoic acid.

6. The dermatological/pharmaceutical composition as defined by claim 5, wherein the concentration of 6-[3-(1-adamantyl)-4-methoxyphenyl]-2-naphthoic acid ranges from about 0.01% to 0.5% by weight relative to the total weight of the composition.

7. The dermatological/pharmaceutical composition as defined by claim 6, wherein the concentration of 6-[3-(1-adamantyl)-4-methoxyphenyl]-2-naphthoic acid is about 0.1% by weight relative to the total weight of the composition.

8. The dermatological/pharmaceutical composition as defined by claim 6, wherein the concentration of 6-[3-(1-adamantyl)-4-methoxyphenyl]-2-naphthoic acid is about 0.3% by weight relative to the total weight of the composition.

9. The dermatological/pharmaceutical composition as defined by claim 1, wherein the benzoyl peroxide concentration ranges from 1 to 10% by weight relative to the total weight of the composition.

10. The dermatological/pharmaceutical composition as defined by claim 9, wherein the benzoyl peroxide concentration ranges from 2.5% to 5% by weight relative to the total weight of the composition.

11. The dermatological/pharmaceutical composition as defined by claim 1, said at least one polyurethane polymer type comprising the polyolprepolymer type 2, the polyolprepolymer type 14 and the polyolprepolymer type 15, or mixture thereof.

12. The dermatological/pharmaceutical composition as defined by claim 11, said at least one polyurethane polymer comprising the polyolprepolymer type 2.

13. The dermatological/pharmaceutical composition as defined by claim 1, wherein the concentration of the polyurethane polymer ranges from 0.5% to 20% by weight relative to the total weight of the composition.

14. The dermatological/pharmaceutical composition as defined by claim 13, wherein the concentration of the polyurethane polymer is 1%, 3% or 5% by weight of the total weight of the composition.

15. The dermatological/pharmaceutical composition as defined by claim 1, formulated as a cream.

16. The dermatological/pharmaceutical composition as defined by claim 1, formulated as a lotion.

17. The dermatological/pharmaceutical composition as defined by claim 1, formulated as a gel cream.

18. The dermatological/pharmaceutical composition as defined by claim 1, further comprising one or more of the following ingredients:
   a) one or more gelling agents or suspending agents,
   b) one or more chelating agents,
   c) one or more wetting agents,
   d) one or more preservatives,
   e) one or more emulsifiers,
   f) one or more wetting surfactants,
   g) one or more lipophilic excipients constituting the fatty phase,
   h) an aqueous phase,
   i) one or more additives.

19. The dermatological/pharmaceutical composition as defined by claim 18, which comprises, in water:
   from 0.1% to 0.3% of a naphthoic acid compound;
   from 1% to 10% of benzoyl peroxide;
   from 1% to 10% of one or more polyurethane polymers;
   from 0.1% to 7% of one or more gelling agents or suspending agents;
   from 0% to 1.5% of one or more chelating agents;
   from 1% to 10% of one or more wetting agents;
   from 0.1% to 20% of an emollient agent;
   from 0.01% to 3% of preservatives; and
   from 0 to 2% of stabilizing agent.

20. The dermatological/pharmaceutical composition as defined by claim 18, which comprises, in water:
   from 0.1% to 0.3% of a naphthoic acid compound;
   from 1% to 10% of benzoyl peroxide;
   from 1% to 10% of one or more polyurethane polymers;
   from 0.1% to 7% of one or more gelling agents or suspending agents;
   from 0% to 1.5% of one or more chelating agents;
   from 1% to 10% of one or more wetting agents;
   from 0.1% to 20% of an emollient agent;
   from 0.1% to 30% of fatty phase;
   from 0% to 3% of preservatives;
   from 0 to 10% of emulsifiers;
   from 0 to 2% of stabilizing agent.

21. The dermatological/pharmaceutical composition as defined by claim 1, formulated as a medicament.

22. A method for the treatment of acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, polymorphic acne, senile acne, solar acne and/or acne medicamentosa, comprising topically applying onto the affected skin area of an individual in need of such treatment, a thus effective amount of a dermatological/pharmaceutical composition as defined by claim 1.

23. The method as defined by claim 22, comprising the treatment of acne vulgaris.

24. A method for formulating a composition as defined by claim 1, comprising the following steps:
   a) mixing the naphthoic acid compound with at least one wetting agent, at least one chelating agent, at least one gelling agent, optionally hydrophilic emulsifiers, and emollients, in water, until said naphthoic acid compound is dispersed, to obtain an active phase 1;
   b) mixing the benzoyl peroxide with at least one wetting agent, at least one chelating agent, at least one gelling agent, optionally hydrophilic emulsifiers, and emollients, in water, until said benzoyl peroxide is dispersed, to obtain an active phase 2;
   c) solubilizing one or more gelling agents other than polyacrylamide, optionally, a chelating agent, one or more preservatives, one or more emollients, one or more emulsifiers, a suspending agent and a stabilizing agent, in water, if necessary in the hot state, while maintaining stirring and optional heating until homogeneity is obtained, to obtain an aqueous phase;
   d) to obtain an emulsion, mixing at least lipophilic emulsifiers, oils and/or solid fatty substances with preservatives, to obtain a fatty phase;
   e) mixing the two active phases obtained respectively in a) and b) to obtain a single active phase;
   f) introducing the said fatty phase obtained in d) into the aqueous phase obtained in c) to obtain an emulsion;

g) adding the single active phase obtained in e) to the emulsion obtained in f) for an emulsion and to the aqueous phase obtained in c) for a gel cream;

h) optionally, introducing polyacrylamide, with stirring, into the product obtained in g) and maintaining stirring until homogeneity is obtained;

i) for a gel cream, introducing oil, with stirring, into the mixture obtained in step g) or h); and j) if necessary, introducing an agent for neutralizing the gelling agent.

25. The method for formulating a composition as defined by claim 24, comprising the following steps:

mixing the active ingredients in the first step of the method, with steps a) and b) being replaced by step a') as described below:

a') mixing the naphthoic acid compound and the benzoyl peroxide with at least one wetting agent, in water, until said benzoyl peroxide and said naphthoic acid compound are dispersed to obtain a single active phase; and continuing the method as described from step c).

26. A topically applicable dermatological/pharmaceutical composition comprising (i) benzoyl peroxide, (ii) 6-[3-(1-adamantyl)-4-methoxyphenyl]-2-naphthoic acid, and (iii) polyolprepolymer type 2; said (i) and (ii) being dispersed in said composition; said (i) and (ii) being present in anti-acne effective amounts and being the only anti-acne agents in said composition; said (i), (ii) and (iii) being formulated into a physiologically acceptable medium as a cream, lotion or gel cream comprising a fatty phase.

27. The dermatological/pharmaceutical composition as defined by claim 26, formulated in the form of a suspension or emulsion with a soft semiliquid or solid consistency of the gel cream type.

* * * * *